US011712583B2

(12) United States Patent
Chao et al.

(10) Patent No.: US 11,712,583 B2
(45) Date of Patent: Aug. 1, 2023

(54) UTILIZING AN OFFSET MULTI-LEAF COLLIMATOR TO IMPROVE DOSE CONFORMALITY AND HOMOGENEITY

(71) Applicant: ACCURAY INCORPORATED, Sunnyvale, CA (US)

(72) Inventors: Edward H. Chao, Sunnyvale, CA (US); Eric Schnarr, McFarland, WI (US); Dylan Casey, Sunnyvale, CA (US)

(73) Assignee: Accuray Incorporated, Sunnyvale, CA (US)

( * ) Notice: Subject to any disclaimer, the term of this patent is extended or adjusted under 35 U.S.C. 154(b) by 218 days.

(21) Appl. No.: 16/916,407

(22) Filed: Jun. 30, 2020

(65) Prior Publication Data
US 2021/0402216 A1 Dec. 30, 2021

(51) Int. Cl.
*A61N 5/10* (2006.01)

(52) U.S. Cl.
CPC ......... *A61N 5/1065* (2013.01); *A61N 5/1031* (2013.01); *A61N 5/1045* (2013.01); *A61N 5/1081* (2013.01); *A61N 5/1083* (2013.01)

(58) Field of Classification Search
CPC .. A61B 6/06; A61B 6/40; A61B 6/405; A61B 6/54; A61B 34/20; A61B 90/10; A61B 6/4405; A61B 6/0407; A61B 6/032; A61B 6/107; A61B 6/037; A61B 6/4258; A61B 18/203; A61B 6/4488; A61B 6/587; A61B 6/547; A61B 6/4035; A61B 6/588; A61B 6/583; A61B 6/586; A61B 6/545; A61B 5/4836; A61B 5/055; A61B 5/0036; A61B 6/4085; A61B 6/4233; A61B 6/42; A61B 6/5205; A61B 6/4266; A61B 6/4441; A61B 6/4447; A61B 5/064; A61B 8/085; A61B 5/0077; A61B 6/584; A61B 6/12; A61B 6/4452; A61B 6/4429; A61B 6/4435; A61B 6/466; A61B 6/482; A61B 6/0414; A61B 6/502; A61N 5/10; A61N 5/103; A61N 5/1031; A61N 5/1036;
(Continued)

(56) References Cited

U.S. PATENT DOCUMENTS

| | | | |
|---|---|---|---|
| 9,324,468 B2 * | 4/2016 | Mansfield | G21K 1/046 |
| 10,888,713 B2 * | 1/2021 | Rieger | G21K 1/043 |

(Continued)

FOREIGN PATENT DOCUMENTS

WO 2015131455 A1 9/2015

OTHER PUBLICATIONS

International Searching Authority, International Search Report dated Sep. 28, 2021 for International Application No. PCT/US2021/036747.

(Continued)

*Primary Examiner* — Irakli Kiknadze
(74) *Attorney, Agent, or Firm* — Womble Bond Dickinson (US) LLP (57) ABSTRACT

A radiation delivery system includes a radiation source to generate a radiation beam to deliver to a target and a multi-leaf collimator (MLC) operatively coupled to the radiation source, wherein the MLC is offset to shift the MLC in a direction relative to a line from the radiation source to a point of interest to cause projections of the radiation beam to be shifted based on the offset.

25 Claims, 9 Drawing Sheets

(58) Field of Classification Search
CPC .. A61N 5/1042; A61N 5/1045; A61N 5/1047;
A61N 5/1048; A61N 5/1064; A61N
5/1065; A61N 5/1067; A61N 5/1077;
A61N 5/1083; A61N 5/1081; A61N
5/1049; A61N 5/1069; A61N 2005/1063;
A61N 2005/1061; A61N 2005/1052;
A61N 5/1043; A61N 5/1039; A61N
2005/1094; A61N 2005/1095; A61N
5/0616; A61N 5/1075; A61N 5/1082;
G21K 1/00; G21K 1/02; G21K 1/025;
G21K 1/04; G21K 1/046; G21K 5/00;
G21K 5/04; G21K 2201/00; G21K 1/043;
G01N 2223/30; G01N 2223/316; G01N
2223/32; G01T 1/1642; G01T 1/1648;
H01J 37/09
USPC .............................................. 378/65, 147–153
See application file for complete search history.

(56) References Cited

U.S. PATENT DOCUMENTS

| | | | |
|---|---|---|---|
| 11,147,989 B2* | 10/2021 | Cox | A61N 5/1036 |
| 2008/0159478 A1* | 7/2008 | Keall | A61N 5/1042 |
| | | | 378/65 |
| 2008/0205597 A1* | 8/2008 | Ono | A61N 5/1042 |
| | | | 378/65 |
| 2010/0128839 A1* | 5/2010 | Partain | A61N 5/1048 |
| | | | 378/65 |
| 2012/0043482 A1* | 2/2012 | Prince | G21K 1/046 |
| | | | 250/505.1 |
| 2012/0256103 A1* | 10/2012 | Luzzara | G21K 1/046 |
| | | | 250/492.1 |
| 2015/0273239 A1 | 10/2015 | Hsu et al. | |
| 2017/0087384 A1 | 3/2017 | Nord et al. | |
| 2017/0143995 A1* | 5/2017 | Bergfjord | G21K 1/046 |
| 2018/0161602 A1* | 6/2018 | Kawrykow | A61N 5/1069 |
| 2018/0243584 A1* | 8/2018 | Nord | A61N 5/1081 |
| 2019/0388711 A1* | 12/2019 | Cox | A61N 5/1081 |
| 2020/0043624 A1 | 2/2020 | Schnarr et al. | |
| 2021/0299473 A1* | 9/2021 | Kaneko | A61N 5/1081 |

OTHER PUBLICATIONS

Greer, P.B. et al. (Oct. 2003). "Improving the resolution of dynamic intensity modulated radiation therapy delivery by reducing the multileaf collimator sampling distance", Med. Phys. 30(10):2793-2803.

Bortheld, T. et al. (Nov. 2000). "What is the optimum leaf width of a multileaf collimator?" Medical Physics 27 (11):2494-2502.

* cited by examiner

UTILIZING AN OFFSET MULTI-LEAF COLLIMATOR TO IMPROVE DOSE CONFORMALITY AND HOMOGENEITY

TECHNICAL FIELD

The present disclosure relates to utilizing an offset multi-leaf collimator (MLC) to improve dose conformality and homogeneity in a radiation delivery system.

BACKGROUND

In radiation treatment, doses of radiation delivered via a radiation treatment beam from a source outside a patient's body are delivered to a target region in the body, in order to destroy tumorous cells. Care must be taken to minimize the amount of radiation that is delivered to non-treatment regions while maximizing the amount of radiation delivered to the intended treatment regions. In radiation treatment, a radiation treatment beam aperture shapes the radiation treatment beam to conform, as closely as possible, to the intended target region. The radiation treatment beam aperture is commonly defined by an MLC.

BRIEF DESCRIPTION OF THE DRAWINGS

The present disclosure will be understood more fully from the detailed description given below and from the accompanying drawings of various implementations of the disclosure.

DETAILED DESCRIPTION

Described herein are embodiments of methods and apparatus for utilizing an offset multi-leaf collimator (MLC) to improve dose conformality and homogeneity. The radiation delivery system may offset an MLC relative to a radiation source to cause the projections of a radiation beam generated by the radiation source to be offset. Offsetting the projections of the radiation beam may result in an improved dose conformality and homogeneity provided to a target region (also referred to as "target" hereafter).

In a radiation delivery system, a radiation source may generate a radiation beam that is to be delivered to a target, such as a tumor. An MLC is coupled to the radiation source that includes leaves that may be used to create one or more patterns that shape the radiation treatment beam to conform to the target. During a treatment session, the radiation source and MLC may be rotated/positioned about a point of interest (which may include the target) by a gantry or robotic arm to deliver doses of radiation to the target from different angles.

In a conventional radiation delivery system, when the MLC is coupled to the radiation source, the MLC is aligned such that the center of the leaves of the MLC is in alignment with a line from the radiation source to a point of interest. In other words, the leaves of the MLC are distributed symmetrically around the line from the radiation source to the point of interest. The alignment of the MLC results in projections of the radiation beam having a spacing that roughly corresponds to the width of the leaves of the MLC. For example, if the leaf width of the MLC is 6.25 millimeters (mm), then the projections of the radiation beam may be spaced approximately 6.25 mm apart. Such a spacing of the projections of the radiation beam may make it difficult to provide a conforming dose of radiation to a target, particularly if the target is relatively small (e.g., less than 3 centimeters (cm)).

Aspects of the disclosure remedy the above and other deficiencies by offsetting an MLC relative to the radiation source. The MLC may be offset relative to the line from the radiation source to the point of interest. The amount of the offset may be based on the width of the leaves in the MLC. In embodiments, the offset may correspond to a quarter leaf offset (e.g., the offset is equal to one-quarter the width of a leaf of the MLC). For example, if the leaf width of the MLC is 6.25 mm, then the offset may be 1.56 mm.

By shifting the MLC relative to the radiation source, the projections of the radiation beam will similarly shift. Additionally, the shifting of the MLC relative to the radiation source may result in opposing projections of the radiation beam. The shift of the MLC and opposing projections may result in the spacing of the projections of the radiation beam to decrease relative to a radiation delivery system utilizing an aligned MLC. For example, rather than having projections of the radiation beam having a spacing that corresponds to the leaf width of the MLC, using an offset MLC may result in having projections of the radiation beam having a spacing that corresponds to half the leaf width of the MLC.

Embodiments of the disclosure provide for an improved radiation delivery system that utilizes an offset MLC to improve dose conformality and homogeneity. The reduced spacing between the projections of the radiation beam allows the radiation delivery system to deliver more conforming doses to a target than conventional radiation delivery systems. Furthermore, the reduced spacing between the projections allows the radiation delivery system to provide the more conforming doses to smaller targets than a conventional radiation delivery system.

Figure 1A:
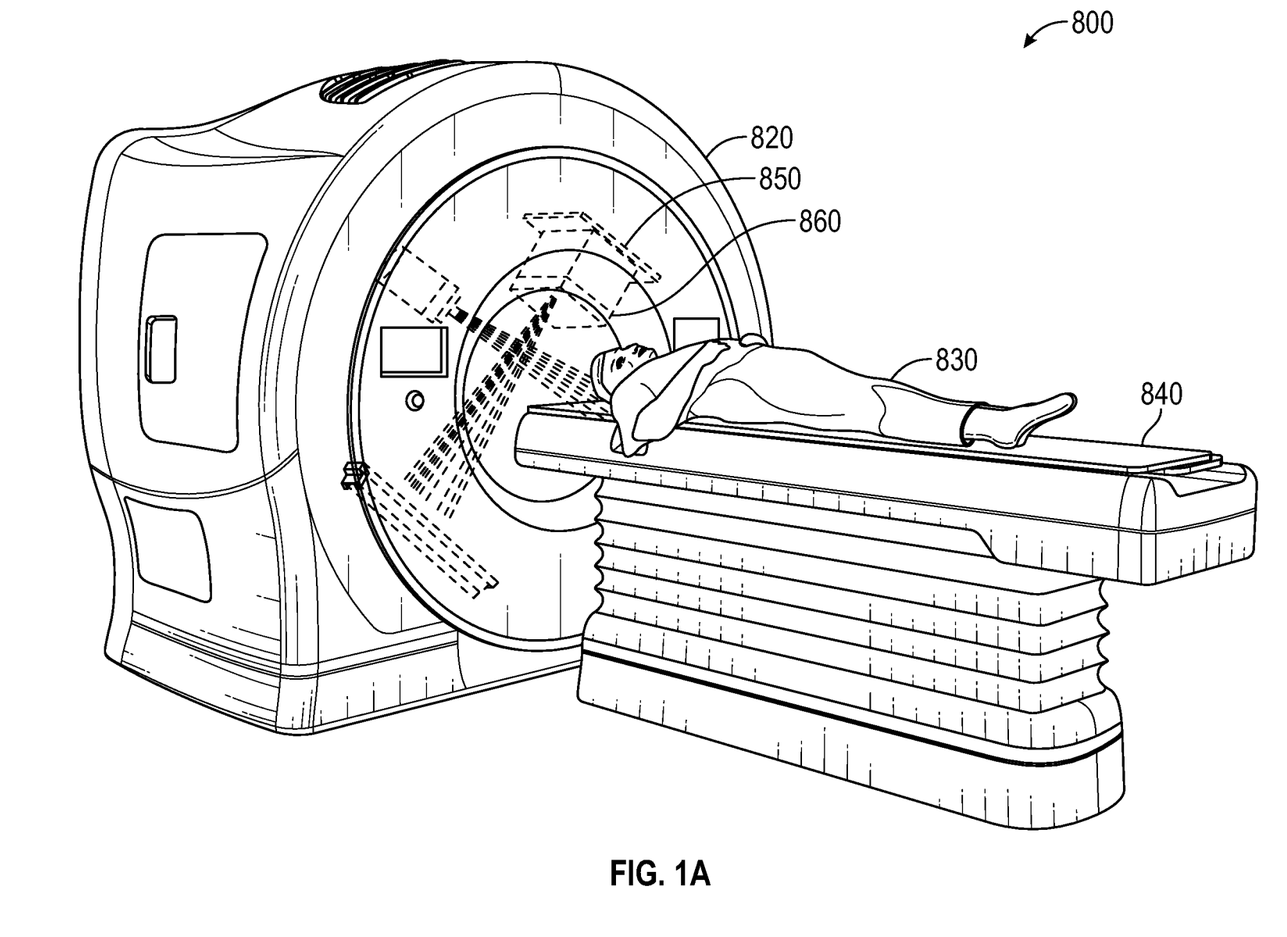
FIG. 1A illustrates a helical radiation delivery system, in accordance with embodiments described herein.

FIG. 1A illustrates a helical radiation delivery system 800 in accordance with embodiments of the present disclosure. The helical radiation delivery system 800 may include a linear accelerator (LINAC) 850 mounted to a ring gantry 820. The LINAC 850 may be used to generate a radiation beam (i.e., treatment beam) by directing an electron beam towards an x-ray emitting target. The treatment beam may deliver radiation to a target region (i.e., a tumor). The treatment system further includes a multileaf collimator (MLC) 860 coupled with the distal end of the LINAC 850. The MLC includes a housing that houses multiple leaves that are movable to adjust an aperture of the MLC to enable shaping of the treatment beam. In embodiments, the MLC 860 may be a binary MLC that includes a plurality of leaves that travel across an entire field width. In an embodiment, the MLC 860 may include a plurality of leaf pairs, arranged in two opposing banks. In some embodiments, the MLC 860 may be an eMLC. In embodiments, MLC 860 may be any other type of MLC. The ring gantry 820 has a toroidal shape in which the patient 830 extends through a bore of the ring/toroid and the LINAC 850 is mounted on the perimeter of the ring and rotates about the axis passing through the center to irradiate a target region with beams delivered from one or more angles around the patient. During treatment, the patient 830 may be simultaneously moved through the bore of the gantry on a treatment couch 840.

Figure 1B:
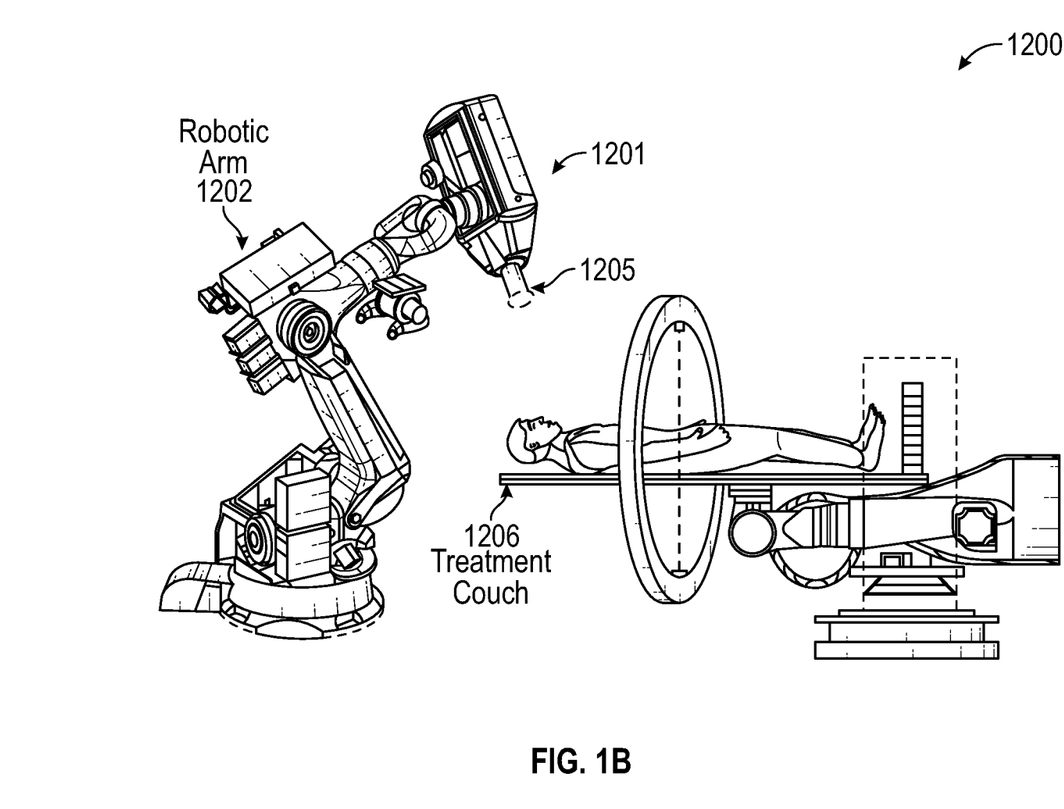
FIG. 1B illustrates a robotic radiation treatment system that may be used in accordance with embodiments described herein.

FIG. 1B illustrates a radiation treatment system 1200 that may be used in accordance with alternative embodiments described herein. As shown, FIG. 1B illustrates a configuration of a radiation treatment system 1200. In the illustrated embodiments, the radiation treatment system 1200 includes a linear accelerator (LINAC) 1201 that acts as a radiation treatment source and an MLC 1205 coupled with the distal end of the LINAC 1201 to shape the treatment beam. In one embodiment, the LINAC 1201 is mounted on the end of a robotic arm 1202 having multiple (e.g., 5 or more) degrees of freedom in order to position the LINAC 1201 to irradiate a pathological anatomy (e.g., target) with beams delivered from many angles, in many planes, in an operating volume around a patient. Treatment may involve beam paths with a single isocenter, multiple isocenters, or with a non-isocentric approach.

LINAC 1201 may be positioned at multiple different nodes (predefined positions at which the LINAC 1201 is stopped and radiation may be delivered) during treatment by moving the robotic arm 1202. At the nodes, the LINAC 1201 can deliver one or more radiation treatment beams to a target, where the radiation beam shape is determined by the leaf positions in the MLC 1205. The nodes may be arranged in an approximately spherical distribution about a patient. The particular number of nodes and the number of treatment beams applied at each node may vary as a function of the location and type of pathological anatomy to be treated.

In another embodiment, the robotic arm 1202 and LINAC 1201 at its end may be in continuous motion between nodes while radiation is being delivered. The radiation beam shape and 2-D intensity map is determined by rapid motion of the leaves in the MLC 1205 during the continuous motion of the LINAC 1201.

Figure 1C:
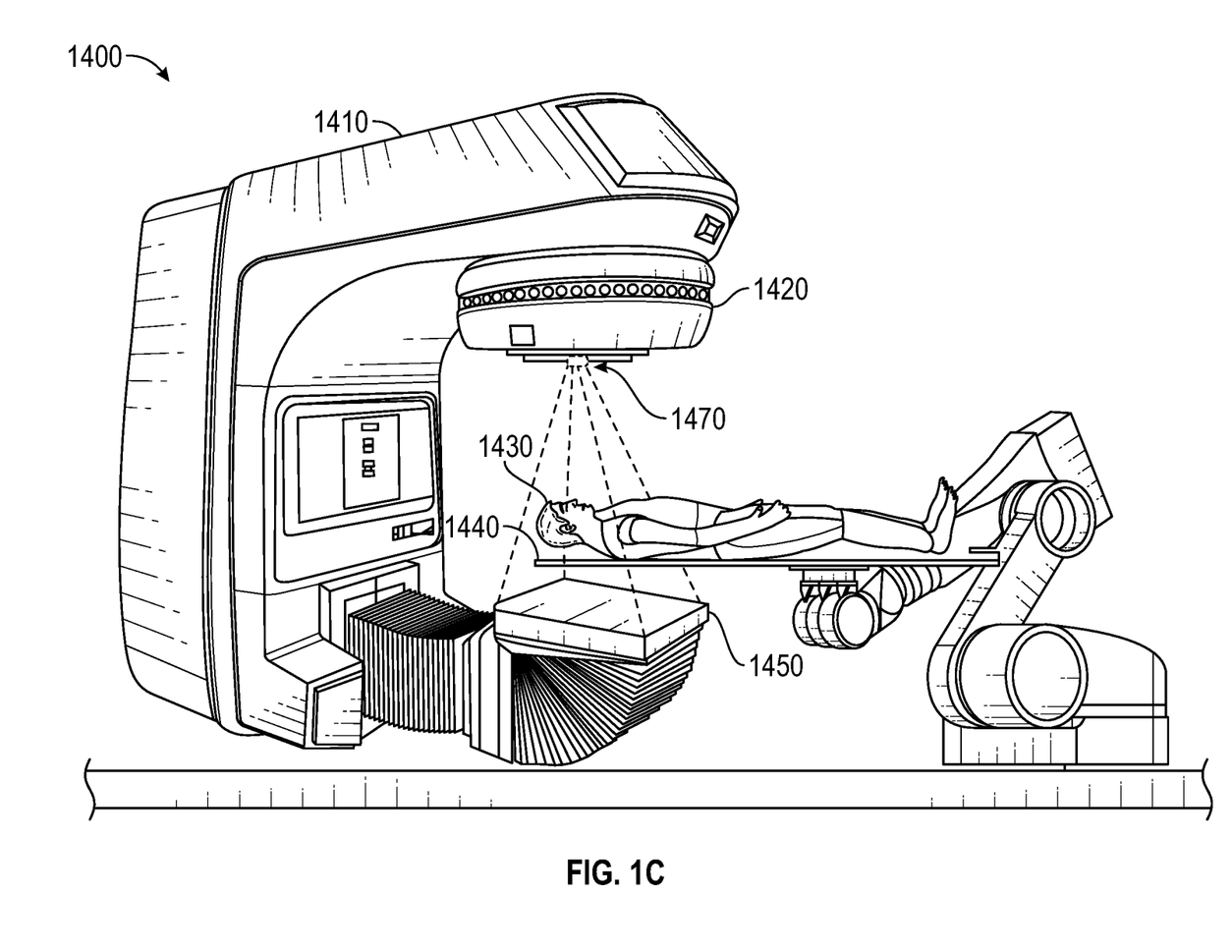
FIG. 1C illustrates a C-arm gantry-based radiation treatment system, in accordance with embodiments described herein.

FIG. 1C illustrates a C-arm radiation delivery system 1400. The system 1400 includes a C-arm gantry 1410, a LINAC 1420, an MLC 1470 coupled with the distal end of the LINAC 1420 to shape the beam, and a portal imaging detector 1450. The C-arm gantry 1410 may be rotated to an angle corresponding to a selected projection and used to acquire an x-ray image of a VOI of a patient 1430 on a treatment couch 1440.

Figure 2A:
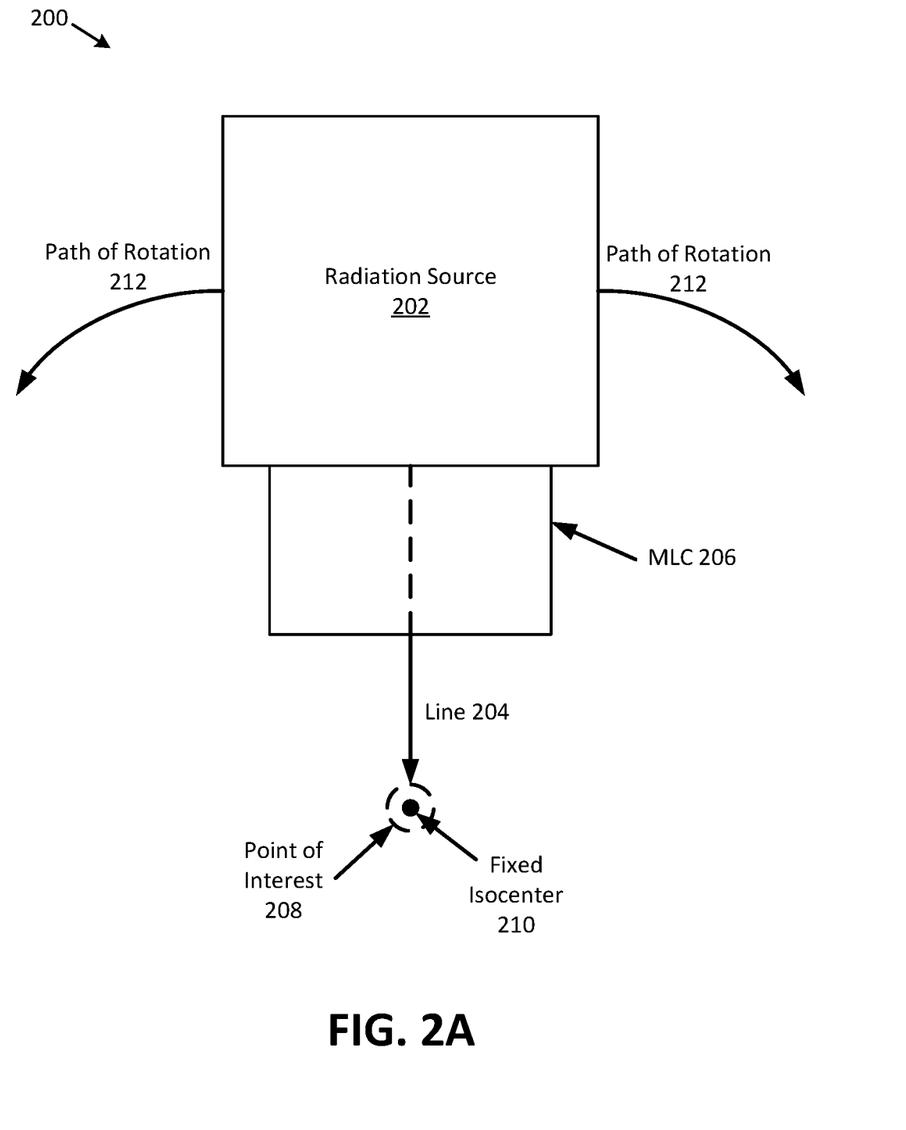
FIG. 2A is an illustration of an example of a radiation delivery system including an aligned MLC, in accordance with embodiments of the disclosure.

FIG. 2A is an illustration of an example of a radiation delivery system 200 including an aligned MLC, in accordance with embodiments of the disclosure. The radiation delivery system 200 includes a radiation source 202 and an MLC 206. In embodiments, radiation source 202 may correspond to LINAC 850 of FIG. 1A. In an embodiment, radiation source 202 may correspond to LINAC 1201 of FIG. 1B. In some embodiments, radiation source 202 may correspond to LINAC 1420 of FIG. 1C. In embodiments, the radiation source 202 may correspond to any type of radiation source configured to generate a radiation beam. In embodiments, the MLC 206 may correspond to MLC 860 of FIG. 1A. In some embodiments, the MLC 206 may correspond to MLC 1205 of FIG. 1B. In an embodiment, the MLC 206 may correspond to MLC 1470 of FIG. 1C.

The point of interest 208 may correspond to a determined position for the direction of a radiation beam generated by the radiation source. In embodiments, the point of interest 208 may be a region of interest (ROI) that includes a target. In embodiments, the point of interest 208 may include a fixed isocenter 210. The fixed isocenter 210 may correspond to a point in space relative to the radiation source 202 about which the radiation source 202 rotates along a path of rotation 212. In embodiments, the radiation source 202 and the MLC 206 may be rotated/positioned about the point of interest 208 by a gantry (e.g., ring gantry 820 of FIG. 1A or C-arm gantry 1410 of FIG. 1C) or a robotic arm (e.g., robotic arm 1202 of FIG. 1B). As previously described, in some embodiments, when the MLC 206 is coupled to the radiation source 202, the MLC 206 is aligned such that the leaves of the MLC 206 are evenly distributed around a line 204 from the radiation source 202 to the point of interest 208.

Figure 2B:
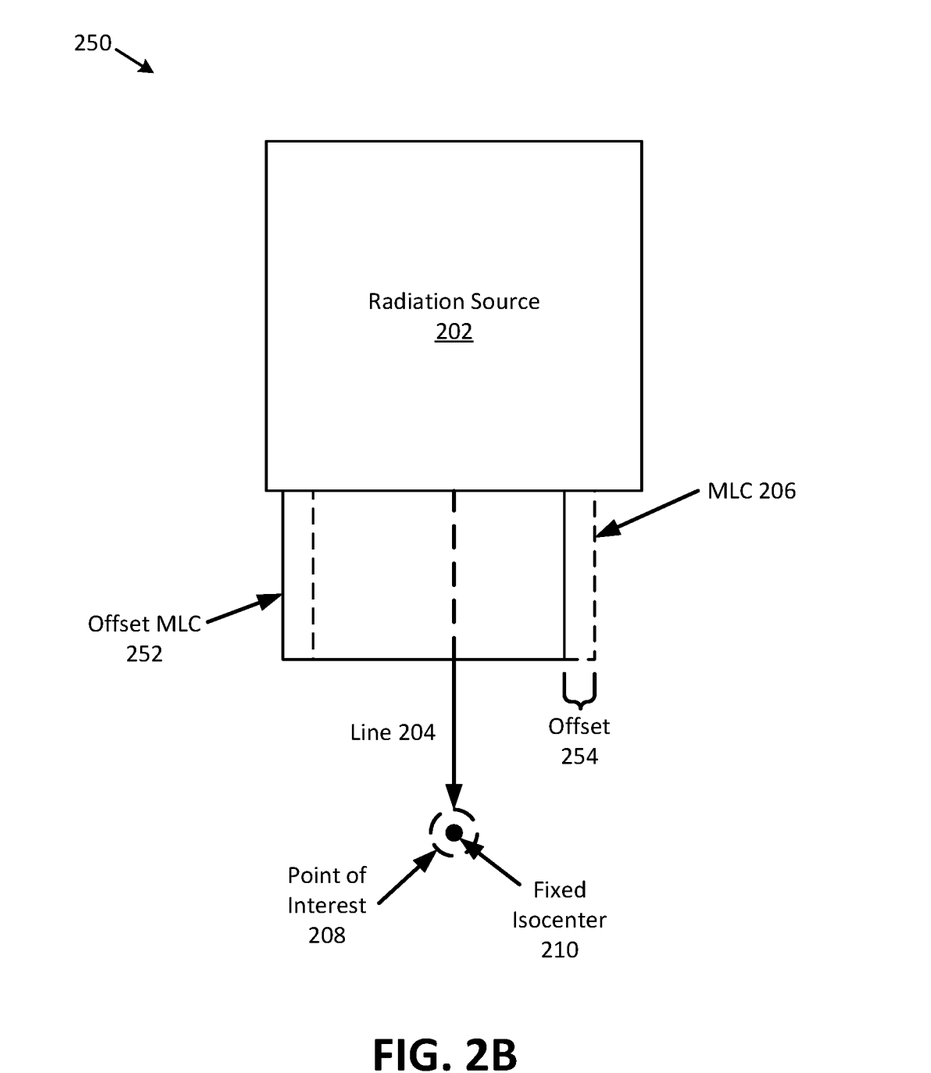
FIG. 2B is an illustration of an example of a radiation delivery system including an offset MLC, in accordance with embodiments of the disclosure.

FIG. 2B is an illustration of an example of a radiation delivery system 250 including an offset MLC, in accordance with embodiments of the disclosure. Radiation delivery system 250 may include similar components to the components of radiation delivery system 200. However, instead of including MLC 206 (represented by dashed lines in FIG. 2B), which is coupled to radiation source 202 in alignment with the line 204 from the radiation source 202 to the point of interest 208, radiation delivery system 250 includes an offset MLC 252.

The offset MLC 252 may be coupled to the radiation source 202, as previously described. However, when the offset MLC 252 is coupled to the radiation source 202, it may be shifted relative to the line 204 by an offset 254. In embodiments, the amount of offset 254 that the offset MLC 252 is shifted by may be based on a leaf width of the leaves of the offset MLC 252. In an embodiment, the amount of offset 254 may correspond to a one-quarter leaf offset (e.g., the amount of offset is ¼ of the leaf width). For example, if the leaf width of the offset MLC 252 is 6.25 mm, then the amount of offset 254 may be 1.56 mm. In embodiments, the amount of offset 254 may correspond to a one-quarter leaf plus or minus one-eighth leaf offset. For example, if the leaf width of the offset MLC 252 is 6.25 mm, then the amount of offset 254 may be 1.56 mm 0.78 mm.

Figure 3:
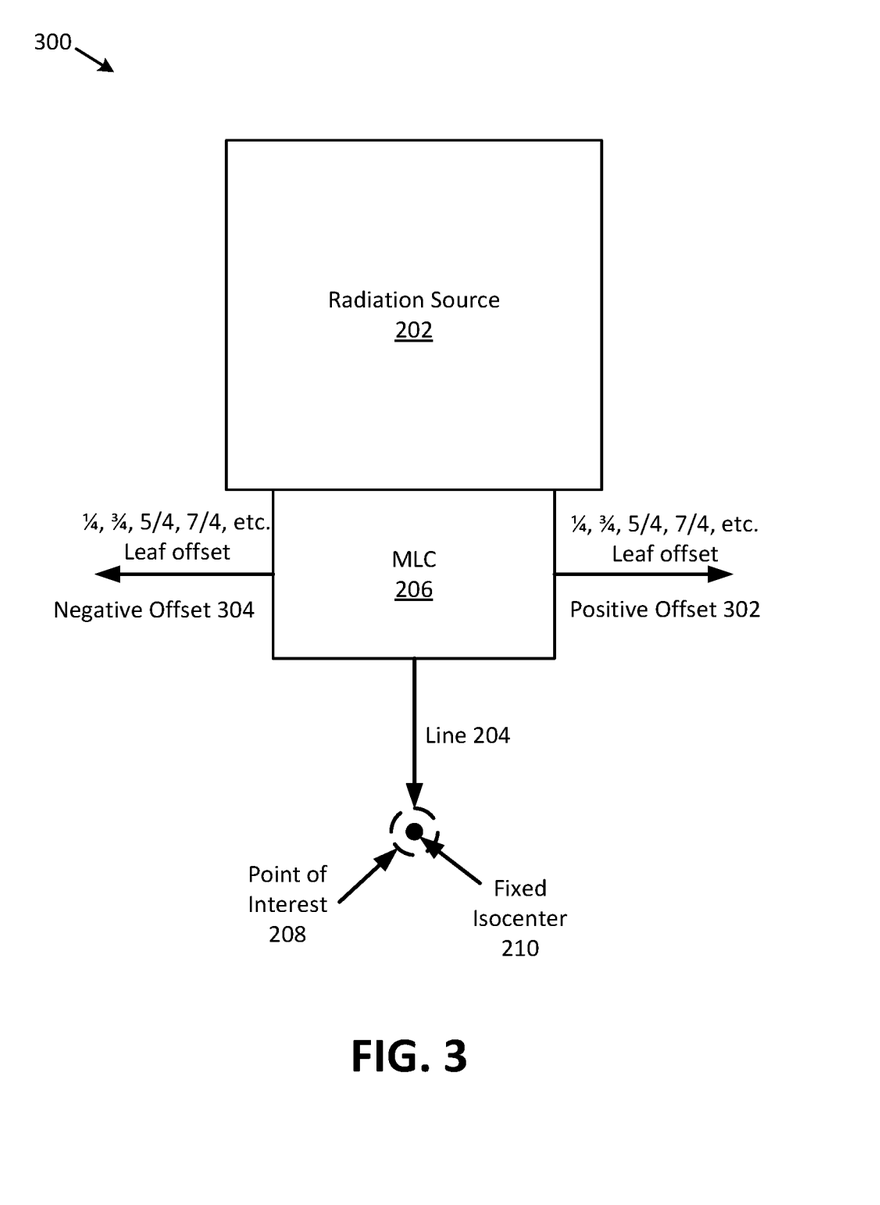
FIG. 3 is an illustration of an example of amounts of offset utilized for an offset MLC of a radiation delivery system, in accordance with embodiments of the disclosure.

FIG. 3 is an illustration of an example of amounts of offset utilized for an offset MLC of a radiation delivery system 300, in accordance with embodiments of the disclosure. Although the embodiment of FIG. 2B described an offset MLC with a quarter leaf offset, embodiments of the disclosure may utilize different offset amounts. Furthermore, embodiments of the disclosure shift the MLC in different directions relative to the line between the radiation source 202 and the point of interest. Radiation delivery system 300 may include radiation source 202, MLC 206, point of interest 208, and fixed isocenter 210, as previously described at FIG. 2A.

In embodiments, the MLC 206 may be shifted using a positive offset 302, which shifts the MLC 206 in a first direction relative to line 204. In an embodiment, the MLC 206 may be shifted using a negative offset 304, which shifts the MLC 206 in a second direction relative to line 204 that is the opposite of the first direction. For example, in FIG. 3 the positive offset 302 may correspond to shifting the MLC 206 to the right, while the negative offset 304 may correspond to shifting the MLC 206 to the left.

Figure 4A:
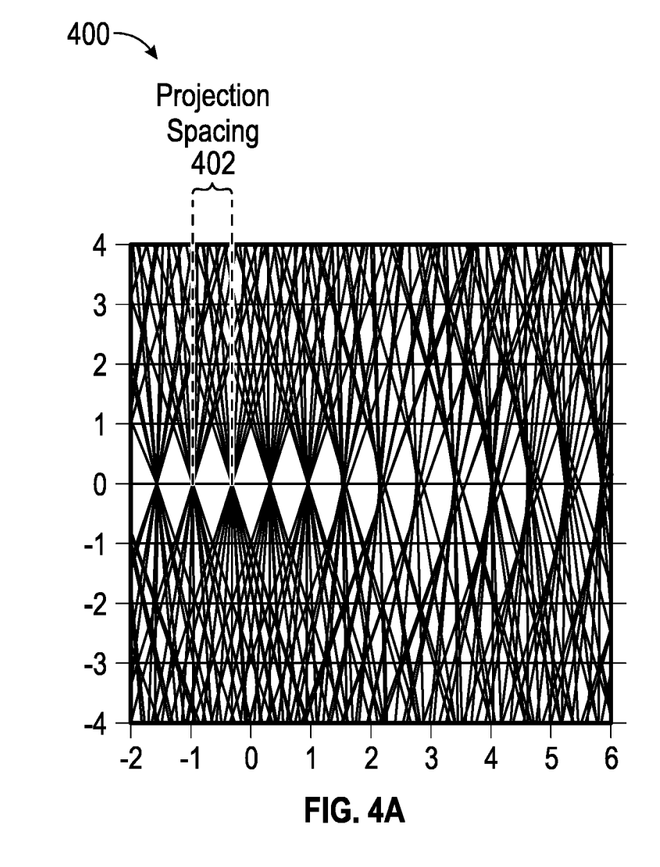
FIG. 4A is an illustration of an example of projections of a radiation beam from an aligned MLC, in accordance with embodiments of the disclosure.
Figure 4B:
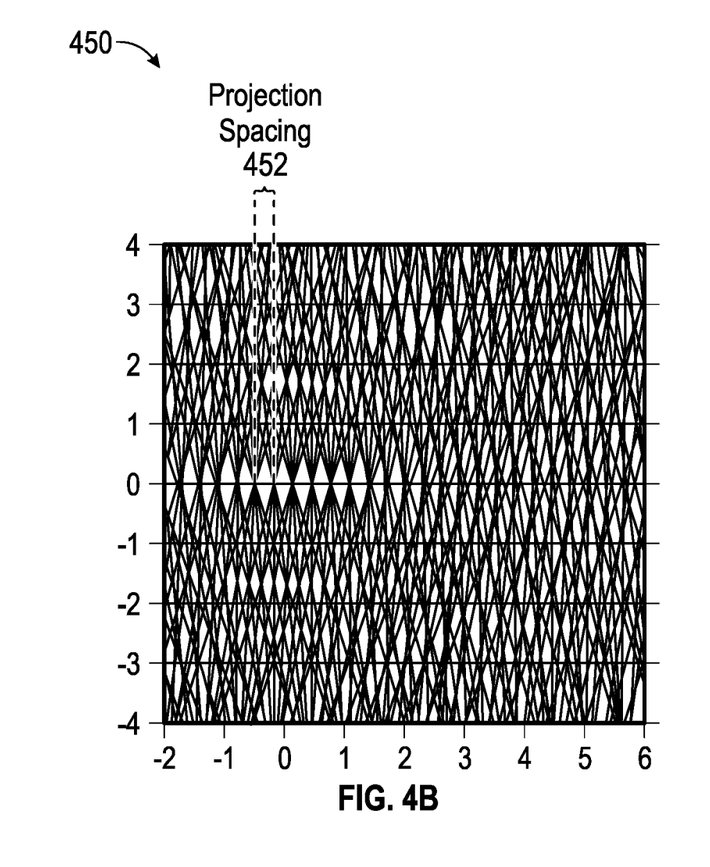
FIG. 4B is an illustration of an example of projections of a radiation beam from an offset MLC, in accordance with embodiments of the disclosure.

In embodiments, the amount of offset may correspond to one of a positive or negative one-quarter plus a positive or negative half integer. For example, the offset may be determined using the following equation:

$$\text{Leaf offset} = \text{Leaf width} \times \left(\frac{1}{4} \pm \frac{N}{2}\right)$$

where Leaf offset may correspond to the amount of offset, Leaf width may correspond to the width of the leaves of MLC 206, and N may correspond to a whole integer. For example, the leaf width may be 6.25 mm and N may be 0, 1, 2, 3, etc. These offset positions describe the ideal MLC placements which will yield the projection spacing shown in FIG. 4B, but small deviations from these offsets will not affect the efficacy. A tolerance of ±⅛ leaf width from each of the ideal offset positions will yield projection spacing that is more similar to FIG. 4B than to 4A.

Offset amounts using different N values may have similar spacing in the projections of the radiation beam because the positioning of the leaves of MLC 206 relative to line 204 may also be similar. For example, an MLC 206 that is shifted using either a positive offset 302 or a negative offset 304 and an offset amount of ¼ of a leaf width, ¾ of a leaf width, 5/4 of a leaf width, 7/4 of a leaf width, etc. may have similar spacing in the projections of the radiation beam generated by the radiation source 202.

FIG. 4A is an illustration 400 of an example of projections of a radiation beam from an aligned MLC, in accordance with embodiments of the disclosure. Illustration 400 may correspond to a square region upon which projections of a radiation beam are received. Each of the lines in illustration 400 may correspond to projections of a radiation beam generated by a radiation source as the radiation source rotates about the square region. For example, the lines in illustration 400 may correspond to projections of the radiation beam as the radiation source rotates from a −20 degree position to a 20 degree position, where the 0 degree position is directly above the square region and projections of the radiation beam as the radiation source rotates from a −160 degree position to a positive 160 degree position, where the 180 degree position is directly below the square region. The lines may be used to illustrate a dose distribution of radiation being provided to a target, such as a tumor, by the radiation beam The illustration 400 includes an X-axis and a Y-axis that correspond to positions within the square region. In embodiments, the coordinates of (0, 0) in illustration 400 may correspond to point of interest (e.g., point of interest 208) and/or a fixed isocenter (e.g., fixed isocenter 210) about which the radiation source is rotated. Near the point of interest (e.g., (0, 0)) is a projection spacing 402 that corresponds to the gap between projections of the radiation beam that are incident upon the square region. In embodiments, the projection spacing 402 when using an aligned MLC may be similar to the leaf width of the leaves of the MLC. For example, if the aligned MLC has a leaf width of 6.25 mm, then the projection spacing 402 may be approximately 6.25 mm.

FIG. 4B is an illustration 450 of an example of projections of a radiation beam from an offset MLC, in accordance with embodiments of the disclosure. Illustration 450 may include similar components to those described in FIG. 4B. However, illustration 450 shows projections of a radiation beam from an offset MLC. Near the point of interest is a projection spacing 452 that corresponds to the gap between projections of the radiation beam that are incident upon the square region. A radiation delivery system utilizing an offset MLC may have a decreased projection spacing 452 when compared to the projection spacing 402 of a radiation delivery system utilizing an aligned MLC. In embodiments, the projection spacing 452 when using an offset MLC may be similar to half of the leaf width of the leaves of the MLC. For example, if the offset MLC has a leaf width of 6.25 mm, then the projection spacing 402 may be approximately 3.12 mm.

Reducing the spacing between projections of the radiation beam may result in improved dose conformality and homogeneity. In embodiments, dose conformality may be determined using a conformality index (CI) that characterizes the degree to which a dose distribution fits a target shape. The CI may be defined as the prescription isodose volume divided by the isodose volume within the target contours using the below equation:

$$CI = V_{Rx}/V_{Rx,T}$$

where $V_{Rx}$ is the volume of the prescription isodose contour, and $V_{Rx,T}$ is the volume of the prescription isodose that is within the target structure. For a prescription isodose volume that perfectly "conforms" or matches the shape of the target volume, the CI has a value of 1. If the isodose volume extends outside of the target volume, the CI value will be greater than one.

In embodiments, homogeneity may be determined using a homogeneity index (HI) that characterizes the amount of dose variation within a target structure. The HI may be determined using the following equation:

$$HI = \frac{Dose_{Max}}{Dose_{Rx}}$$

where $Dose_{Max}$ is the maximum dose in the target structure and $Dose_{Rx}$ is the prescription dose.

Figure 5:
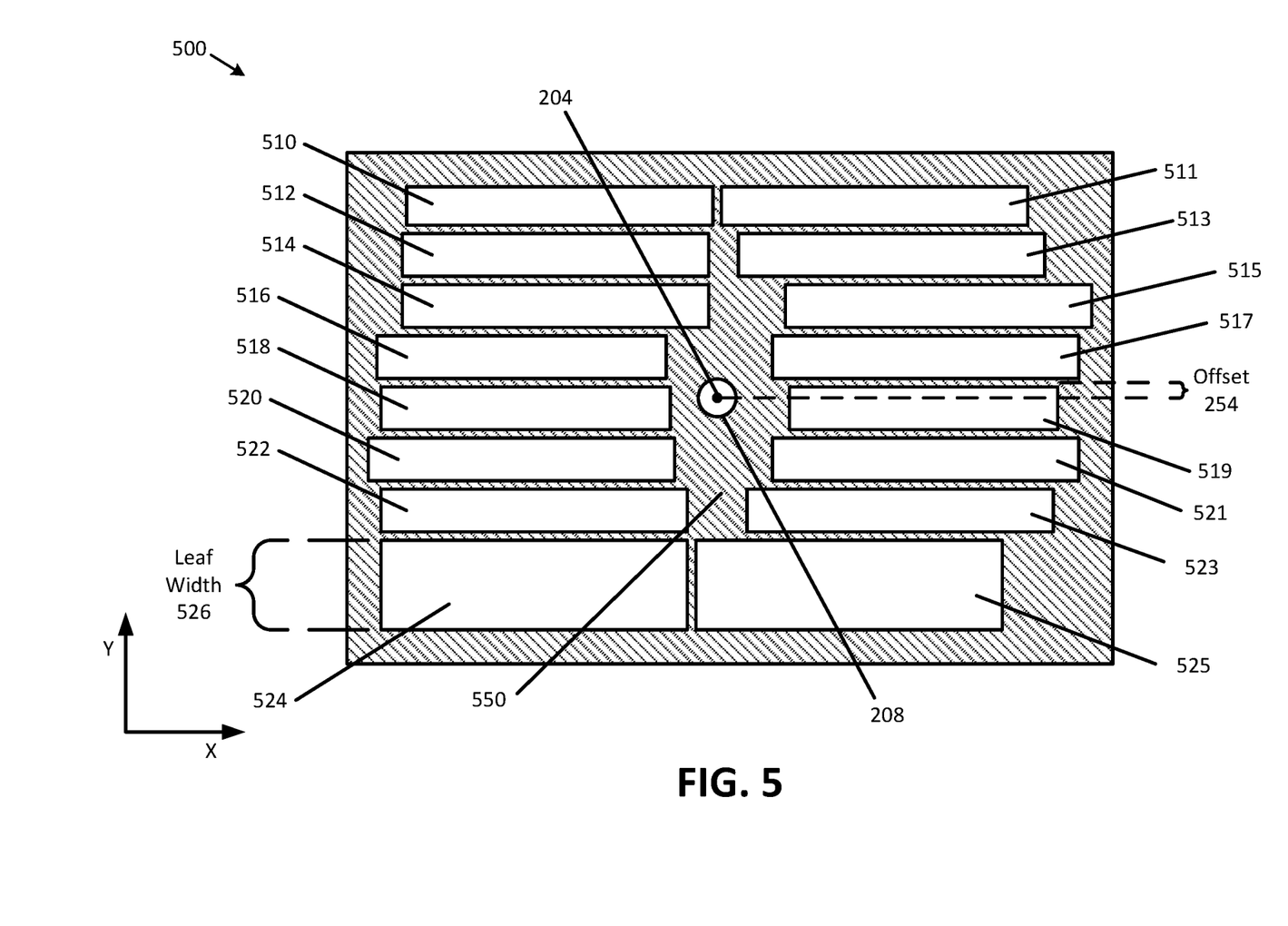
FIG. 5 illustrates an example of an MLC having end leaves of a differing width, in accordance with embodiments of the disclosure.

FIG. 5 illustrates an example of an MLC 500 having end leaves of a differing width, in accordance with embodiments of the disclosure. MLC 500 includes 8 leaf pairs (510-525) in various positions within the MLC 500. The positions of leaf pairs 510-525 may form opening 550, which may be used to shape a radiation beam generated by a radiation source. For example, the leaf pairs 510-525 may form an opening 550 that corresponds to a shape of a target region. In a conventional MLC, leaf pairs 510-525 may all have similar leaf widths. For example, in a conventional MLC, each of leaves 510-525 may have a leaf width of 6.25 mm.

FIG. 5 includes the point of interest 208, line 204, and offset 254, as previously described at FIGS. 2A and 2B. In FIG. 5, line 204 may be substantially parallel with a Z-axis that is perpendicular to the X-Y plane of FIG. 5. The offset 254 may shift the MLC 500 along the Y-axis of FIG. 5. In FIG. 5, the offset 254 corresponds a negative offset (e.g., negative offset 304 of FIG. 3), where the MLC 500 is shifted in a negative direction relative to the Y-axis. However, in embodiments the offset 254 may correspond to a positive offset (e.g., positive offset 302 of FIG. 3), where the MLC is shifted in a positive direction relative to the Y-axis.

Referring to FIG. 5, MLC 500 includes end leaves 524, 525 that each have a corresponding leaf width 526 that is different than the other leaves (e.g., leaves 510-523) of the MLC 500. For example, end leaves 524, 525 may have corresponding leaf widths 526 that are greater than the leaf widths of the other leaves of the MLC 500. Having end leaves 524, 525 with a different leaf width 526 may permit MLC 500 as a whole to be aligned symmetrically relative to line 204 while allowing leaves 510-525 to be offset (e.g., aligned asymmetrically) about the point of interest 208 and/or line 204. Allowing the whole MLC 500 to be symmetric about the point of interest 208 and/or line 204 may improve the performance of the radiation delivery system if the radiation source is used to generate an MV (or kV) imaging beam by balancing X-ray projections on both ends of MLC 500.

In embodiments, the leaf width 526 of end leaves 524, 525 may be greater than the leaf width of end leaves 510, 511 of MLC 500. In an embodiments, the leaf width 526 may be based on an offset of the MLC relative to the radiation source, as previously described. In some embodiments, the leaf width 526 may be equal to the leaf width of the other leaves of MLC 500, plus or minus twice the offset amount. For example, in an MLC having a standard leaf width of 6.25 mm and a desired offset of 1.56 mm (e.g., quarter leaf), then the leaf width may be 6.25 mm±3.12 mm (e.g., two times the desired offset).

Figure 6:
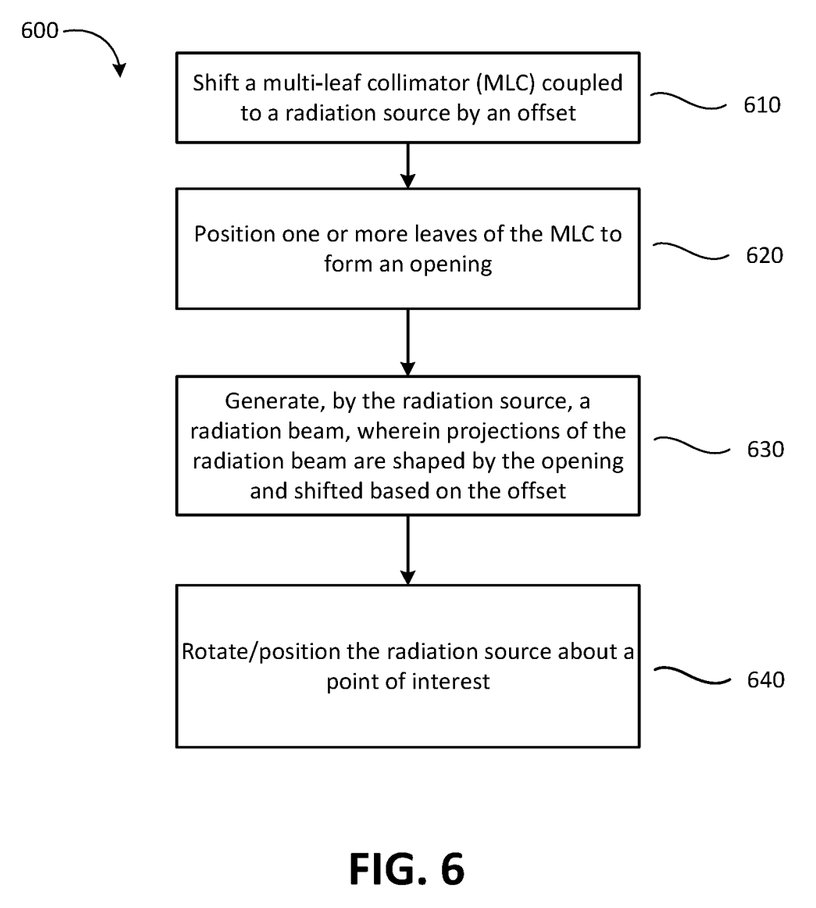
FIG. 6 depicts a flow diagram of a method of utilizing an offset MLC to improve dose conformality and homogeneity, in accordance with embodiments of the disclosure.

FIG. 6 depicts a flow diagram of a method 600 of utilizing an offset MLC to improve dose conformality and homogeneity, in accordance with embodiments of the disclosure. In embodiments, various portions of method 600 may be performed by a radiation delivery system, such as the radiation delivery systems described at FIGS. 1A-3.

With reference to FIG. 6, method 600 illustrates example functions used by various embodiments. Although specific function blocks ("blocks") are disclosed in method 600, such blocks are examples. That is, embodiments are well suited to performing various other blocks or variations of the blocks recited in method 600. It is appreciated that the blocks in method 600 may be performed in an order different than presented, and that not all of the blocks in method 600 may be performed.

Method 600 begins at block 610, where a multi-leaf collimator (MLC) coupled to a radiation source is shifted by an offset. In embodiments, the offset may be based on a leaf width of one or more leaves of the MLC, as previously described.

At block 620, one or more leaves of the MLC are positioned to form an opening.

At block 630, the radiation source generates a radiation beam. Projections of the radiation beam are shaped by the opening formed by the leaves of the MLC and shifted based on the offset.

At block 640, the radiation source is rotated/positioned about a point of interest. In embodiments, the radiation source may be rotated/positioned along a path of rotation. In an embodiment, the radiation source may be rotated about the point of interest by a gantry, such as a ring or C-arm gantry. In embodiments, the radiation source may be positioned about the point of interest by a robotic arm. In some embodiments, the point of interest may include a fixed isocenter, as previously described.

It should be noted that the methods and apparatus described herein are not limited to use only with medical treatment. In alternative implementations, the methods and apparatus herein may be used in applications outside of the medical technology field, such as industrial imaging and non-destructive testing of materials. In such applications, for example, "treatment" may refer generally to the effectuation of an operation controlled by the treatment planning system, such as the application of a beam (e.g., radiation, acoustic, etc.) and "target" may refer to a non-anatomical object or area.

The preceding description sets forth numerous specific details such as examples of specific systems, components, methods, and so forth, in order to provide a good understanding of several embodiments of the present disclosure. It will be apparent to one skilled in the art, however, that at least some embodiments of the present disclosure may be practiced without these specific details. In other instances, well-known components or methods are not described in detail or are presented in simple block diagram format in order to avoid unnecessarily obscuring the present disclosure. Thus, the specific details set forth are merely exemplary. Particular embodiments may vary from these exemplary details and still be contemplated to be within the scope of the present disclosure.

Reference throughout this specification to "one embodiment" or "an embodiment" means that a particular feature, structure, or characteristic described in connection with the embodiments included in at least one embodiment. Thus, the appearances of the phrase "in one embodiment" or "in an embodiment" in various places throughout this specification are not necessarily all referring to the same embodiment.

Although the operations of the methods herein are shown and described in a particular order, the order of the operations of each method may be altered so that certain operations may be performed in an inverse order or so that certain operation may be performed, at least in part, concurrently with other operations. In another embodiment, instructions or sub-operations of distinct operations may be in an intermittent or alternating manner.

The above description of illustrated implementations of the invention, including what is described in the Abstract, is not intended to be exhaustive or to limit the invention to the precise forms disclosed. While specific implementations of, and examples for, the invention are described herein for illustrative purposes, various equivalent modifications are possible within the scope of the invention, as those skilled in the relevant art will recognize. The words "example" or "exemplary" are used herein to mean serving as an example, instance, or illustration. Any aspect or design described herein as "example" or "exemplary" is not necessarily to be construed as preferred or advantageous over other aspects or designs. Rather, use of the words "example" or "exemplary" is intended to present concepts in a concrete fashion. As used in this application, the term "or" is intended to mean an inclusive "or" rather than an exclusive "or". That is, unless specified otherwise, or clear from context, "X includes A or B" is intended to mean any of the natural inclusive permutations. That is, if X includes A; X includes B; or X includes both A and B, then "X includes A or B" is satisfied under any of the foregoing instances. In addition, the articles "a" and "an" as used in this application and the appended claims should generally be construed to mean "one or more" unless specified otherwise or clear from context to be directed to a singular form. Moreover, use of the term "an embodiment" or "one embodiment" or "an implementation" or "one implementation" throughout is not intended to mean the same embodiment or implementation unless described as such. Furthermore, the terms "first," "second," "third," "fourth," etc. as used herein are meant as labels to distinguish among different elements and may not necessarily have an ordinal meaning according to their numerical designation.

What is claimed is:

1. A radiation delivery system, comprising:
   a radiation source to generate a radiation beam to deliver to a target, wherein a line extends from the radiation source to a point of interest including the target; and
   a multi-leaf collimator (MLC) operatively coupled to the radiation source, wherein the radiation source and the MLC move along a path of rotation about the point of interest, and wherein the MLC is offset to shift the MLC by a positive or negative one-quarter leaf width in a direction parallel to the path of rotation and perpendicular to the line to cause projections of the radiation beam to be shifted based on the offset.

2. The radiation delivery system of claim 1, wherein the radiation beam comprises a megavolt (MV) treatment beam.

3. The radiation delivery system of claim 1, wherein the offset corresponds to a positive or negative one-quarter plus a positive or negative half integer leaf width.

4. The radiation delivery system of claim 3, wherein the offset comprises a tolerance, wherein the tolerance corresponds to up to a positive or negative one-eighth leaf width.

5. The radiation delivery system of claim 1, wherein the point of interest comprises a fixed isocenter.

6. The radiation delivery system of claim 1, further comprising:
   a gantry coupled to the radiation source, wherein the gantry is configured to rotate the radiation source about the point of interest.

7. The radiation delivery system of claim 6, wherein the gantry comprises a C-arm gantry.

8. The radiation delivery system of claim 6, wherein the gantry comprises a ring gantry.

9. The radiation delivery system of claim 1, further comprising:
   a robotic arm coupled to the radiation source, wherein the robotic arm is configured to position the radiation source at a plurality of positions along a circular or elliptical trajectory.

10. The radiation delivery system of claim 9, wherein the robotic arm positions the radiation source at the plurality of positions about the point of interest.

11. The radiation delivery system of claim 1, wherein the radiation beam comprises a kilovolt (kV) treatment beam.

12. The radiation delivery system of claim 1, wherein the MLC comprises a binary MLC.

13. The radiation delivery system of claim 1, wherein the MLC comprises an end leaf having a width that is greater than other leaves of the MLC.

14. A method comprising:
   moving a multi-leaf collimator (MLC) coupled to a radiation source by an offset corresponding to a positive or negative one-quarter leaf width in a direction parallel to a path of rotation about a point of interest and perpendicular to a line from the radiation source to the point of interest;
   positioning one or more leaves of the MLC to form an opening; and
   generating, by the radiation source, a radiation beam, wherein projections of the radiation beam are shaped by the opening of the MLC and the projections of the radiation beam are shifted based on the offset.

15. The method of claim 14, wherein the offset corresponds to a positive or negative one-quarter plus a positive or negative half integer leaf width.

16. The method of claim 15, wherein the offset comprises a tolerance, wherein the tolerance corresponds to up to a positive or negative one-eighth leaf offset.

17. The method of claim 14, further comprising:
   rotating, by a gantry coupled to the radiation source, the radiation source about the point of interest.

18. The method of claim 17, wherein the point of interest comprises a fixed isocenter.

19. The method of claim 17, wherein the gantry comprises a C-arm gantry.

20. The method of claim 17, wherein the gantry comprises a ring gantry.

21. The method of claim 14, further comprising:
   positioning, by a robotic arm coupled to the radiation source, the radiation source at a plurality of positions along a circular or elliptical trajectory about the point of interest.

22. A multi-leaf collimator (MLC), comprising:
   a plurality of leaves configured to move independently in a first direction to shape a beam of a radiation source, wherein an end leaf of the plurality of leaves has a width that is different than other leaves of the plurality of leaves, and wherein the plurality of leaves are configured to move by an offset corresponding to a positive or negative one-quarter width of a leaf of the other leaves of the plurality of leaves in a second direction perpendicular to the first direction and parallel to a path of rotation about a point of interest.

23. The MLC of claim 22, wherein the width of the end leaf is greater than a second width of a second end leaf of the plurality of leaves.

24. The MLC of claim 22, wherein the width is based on an offset of the MLC relative to the radiation source.

25. The MLC of claim 24, wherein the offset corresponds to a one-quarter plus or minus one-eighth leaf offset.

* * * * *